United States Patent [19]
Wan

[11] Patent Number: 5,846,213
[45] Date of Patent: Dec. 8, 1998

[54] CELLULOSE MEMBRANE AND METHOD FOR MANUFACTURE THEREOF

[75] Inventor: Wan-Kei Wan, Sarnia, Canada

[73] Assignee: The University of Western Ontario, London, Canada

[21] Appl. No.: 876,400

[22] Filed: Jun. 16, 1997

[51] Int. Cl.$^6$ ............ A61F 13/00; B01D 39/18; A61L 15/28
[52] U.S. Cl. .......... 602/49; 210/500.25; 210/500.29; 210/655; 435/101; 435/252.1; 435/823; 424/445; 424/488; 602/43; 602/49; 536/56; 604/289; 604/304; 604/308; 604/374
[58] Field of Search .................. 435/101, 823, 435/252.1; 536/56; 210/500.29, 500.25, 655; 424/488, 445; 604/289, 304, 308, 374; 602/43, 48, 49

[56] References Cited

U.S. PATENT DOCUMENTS

| | | | |
|---|---|---|---|
| 4,333,972 | 6/1982 | Kesting | 427/244 |
| 4,378,431 | 3/1983 | Brown | 435/101 |
| 4,655,758 | 4/1987 | Ring et al. | 604/374 |
| 4,745,058 | 5/1988 | Townsley | 435/262 |
| 4,788,146 | 11/1988 | Ring et al. | |
| 4,857,201 | 8/1989 | Black et al. | 210/655 |
| 4,863,565 | 9/1989 | Johnson et al. | 435/101 |
| 4,912,049 | 3/1990 | Farah | |
| 4,942,128 | 7/1990 | Brown | 435/101 |
| 5,079,162 | 1/1992 | Ben-Bassat et al. | |
| 5,108,383 | 4/1992 | White | 604/368 |
| 5,144,021 | 9/1992 | Arie et al. | 536/56 |
| 5,273,891 | 12/1993 | Westland et al. | 106/162.5 |

*Primary Examiner*—Herbert J. Lilling
*Attorney, Agent, or Firm*—Lynn C. Schumacher; Hill & Schumacher; Dowell & Dowell, P.C.

[57] ABSTRACT

Cellulose films useful as wound and burn dressings are prepared from a solution of cellulose produced by *Acetobacter xylinum* in a stirred tank. The materials of this invention comprise a film of microbially produced cellulose, particularly cellulose produced from the culture of *Acetobacter xylinum* in a stirred tank. The film is made by dissolving the cellulose in a solvent system comprising dimethylacetamide and lithium chloride, casting the resulting solution onto a flat surface and regenerating the film in a gelation bath. Humectant is incorporated into the film by solvent exchange. The film is then sterilized and packaged for long term storage. These films are strong and elastic having mechanical properties superior to plant derived cellulose membranes and similar to that of the human skin and are useful as wound dressings.

25 Claims, 6 Drawing Sheets

CELLULOSE MEMBRANE AND METHOD FOR MANUFACTURE THEREOF

FIELD OF THE INVENTION

The present invention relates to a method for the preparation of a microbial cellulose membrane.

BACKGROUND OF THE INVENTION

For the treatment of burns, abrasions and surgical incisions, a variety of products are currently available. The commonest type being the medicated gauze-type dressing. This type of dressing requires frequent changes to observe the healing process and to apply medication to the wound. This is often accompanied by discomfort to the patient since some adherence to the wound or wound exudate is common. More importantly, gauze-type dressings do not protect the wound from bacterial infection and as well lack moisture balance for proper healing of the wound.

More recently, various polymeric materials have been investigated for wound dressing application. These can be subdivided into two broad classes of materials, the first consisting of synthetic polymeric materials such as polyurethanes and the other consisting of naturally derived polymeric materials such as collagen. Wound dressings have been made using combinations of materials from these two classes of materials. Some of the currently available products are described in the following papers: "Principles of Burn Dressings" in Biomaterials, volume 6, p.369–377, 1985 by Quinn, Courtney, Evans and Gaylor; and "Modern Dressings: What to Use" in Australian Family Physician, volume 23, p.824–839, 1994.

The production of cellulose pellicles by the bacteria *Acetobacter xylinum* and their conversion into liquid loaded pads for use as wound dressing was disclosed in U.S. Pat. No. 4,788,146. Liquids loaded include various medications that are deemed useful in various functions in the process of wound healing.

U.S. Pat. No. 4,912,049 describes a process for the production of cellulose pellices from the bacteria Acetobacter xylinum and their processing into thin sheets for biomedical applications. This patent forms the basis of a commercial wound dressing product Biofill™. This product has been shown to be effective in the treatment of a variety of wounds. However, a drawback to this material is that it is prone to being easily torn, especially when applied to areas of mobility on the body due to lack of sufficient elasticity of the material.

The production of cellulose by the bacteria *Acetobacter xylinium* has been studied by numerous investigators. Their interests have been mainly on the cellulose generation mechanism of the bacterial. In a static reactor, cellulose pellicles are formed at the air/liquid medium interface. The cellulose fibers formed under such condition have nominally infinite length and are intertwined together to form a pellicle. However, under agitation the cellulose fibers are broken up into microfibrils. The dimensions of the microfibrils are a function of the reaction conditions. Production of cellulose fibrils is described in U.S. Pat. Nos. 5,079,162 and 5,144,021 and a paper entitled "Properties and Uses of Bacterial Cellulose Produced in Fermenters" presented by Johnson, Stephens and Westland in the American Chemical Society Meeting in April, 1990. An advantage of bacterial produced cellulose is that a high degree of control over product purity can be obtained in comparison to other non-bacterial methods of cellulose production. In addition, control over the size and porosity of the cellulose is important for medical end uses due to the need to incorporate other medicinal agents into the dressing.

Cellulose fibrils formed by *Acetobacter xylinum* (*A. xylinum*) are much smaller than cellulose fibers from the standard pulping of wood as shown in Table 1.

TABLE 1

| Cellulose Fiber Dimensions | | |
|---|---|---|
| Source | Length | Width |
| A. xylinum cellulose | ~30 µm | 0.1–0.2 µm |
| Birch | 0.8–1.6 mm | 14–40 µm |
| Pine | 2.6–4.4 mm | 30–75 µm |

These lower molecular weight cellulose materials are much more desirable than other sources of heavier molecular weight cellulose since the former are in principle more readily worked with due to their lower molecular weight than plant source cellulose. Cellulose fibers derived from plant sources can be dissolved in several solvent systems to form highly viscous solutions. These solutions form the basis of the regenerated cellulose fibre industry. Practical cellulose dissolution processes are described in the "Kirk-Othmer Encyclopedia of Chemical Technology", Fourth Edition 1993, volume 5, p.476–563. These include the viscose process in which cellulose xanthate derivatives are formed and the cuen process which depends on the formation of copper complexes with cellulose. Due to the nature of these solvent systems, cellulose dissolved in these solvent systems tend to degrade over time. A non-degrading solvent system for cellulose comprising dimethylacetamide and lithium chloride was described in an article entitled "Solution Studies of Cellulose In Lithium Chloride and Dimethylacetamide" in Macromolecules, volume 18, p.2394–2401, 1985 by McCormick, Callais and Hutchinson, Jr. and U.S. Pat. No. 4,857,201. Although these solvent systems are suitable for cellulose of plant origin, they heretofore have not been applied to microbially produced cellulose.

Currently, a variety of substances and procedures exist for the treatment of wounds. Research over the years has led to a consensus on the ideal characteristics of wound dressings. It is agreed that a wound covering should be adherent, elastic, pliable, impermeable to bacteria, easy to handle, non-toxic, allow for proper water vapour permeability for moisture balance and possess mechanical properties so it can be used on areas of high movement. The wound dressings available today all attempt to meet the criteria of an ideal wound dressing but such a dressing is yet to be developed. It would be very advantageous to provide a method for producing membranes for wound dressings from bacterially-produced cellulose. Cellulose membranes and films can be made by casting these solutions onto a flat surface.

OBJECTIVES OF THE INVENTION

An objective of the present invention is to provide a bacterially produced cellulose membrane, and method for production, that may be used as a wound dressing that is effective in providing a favourable environment for the healing of the wound. Another objective is to provide a cellulose membrane that has good mechanical properties including flexibility, similar to the mechanical properties of human skin, and can be used effectively in areas of high mobility. Still a further objective is to provide a wound dressing that can be used on large area wounds. Another further objective is to provide a process for the preparation of the aforementioned cellulose membrane. These and other objectives will readily become apparent to those skilled in the art in view of the teachings hereinafter set forth.

SUMMARY OF THE INVENTION

The materials of this invention comprise a film of microbially produced cellulose, particularly cellulose produced from the culture of *Acetobacter xylinum* in a stirred tank. The film is made by dissolving the cellulose in a solvent system comprising dimethylacetamide and lithium chloride, casting the resulting solution onto a flat surface and regenerating the film in a gelation bath. Humectant is incorporated into the film by solvent exchange. The film is then depyrogenated, sterilized and packaged for long term storage.

In one aspect of the invention there is provided a method for producing a cellulose membrane from microbially produced cellulose. The method comprises the steps of providing a microbially produced cellulose; dissolving the cellulose into a solvent system comprising a lithium salt and dimethylacetamide; casting the solution onto a surface and drying to produce a membrane; coagulating the membrane in a gelation bath; and incorporating a humectant into the membrane by solvent exchange.

In this aspect of the invention the lithium salt is preferably lithium chloride. The microbially produced cellulose is preferably produced by the bacteria *Acetobacter xylinum*.

In another aspect of the invention there is provided a cellulose membrane useful as a wound dressing. The membrane is produced by a process comprising the steps of providing a microbially produced cellulose; dissolving the cellulose into a solvent system comprising a lithium salt and dimethylacetamide; casting the solution onto a surface and drying to produce a membrane; coagulating the membrane in a gelation bath; and incorporating a humectant into the membrane by solvent exchange.

In another aspect of the invention there is provided a wound dressing comprising a microbially produced cellulose membrane and a humectant incorporated into the membrane. In this aspect of the invention the microbially produced cellulose may be produced by the bacteria *Acetobacter xylinum*.

BRIEF DESCRIPTION OF THE DRAWINGS

The product wound dressing and method of producing the wound dressing in accordance with the present invention will now be described, by way of example only, reference being had to the accompanying drawings, in which.

DETAILED DESCRIPTION OF THE INVENTION

Cellulose Dissolution and Preparation

Figure 1:
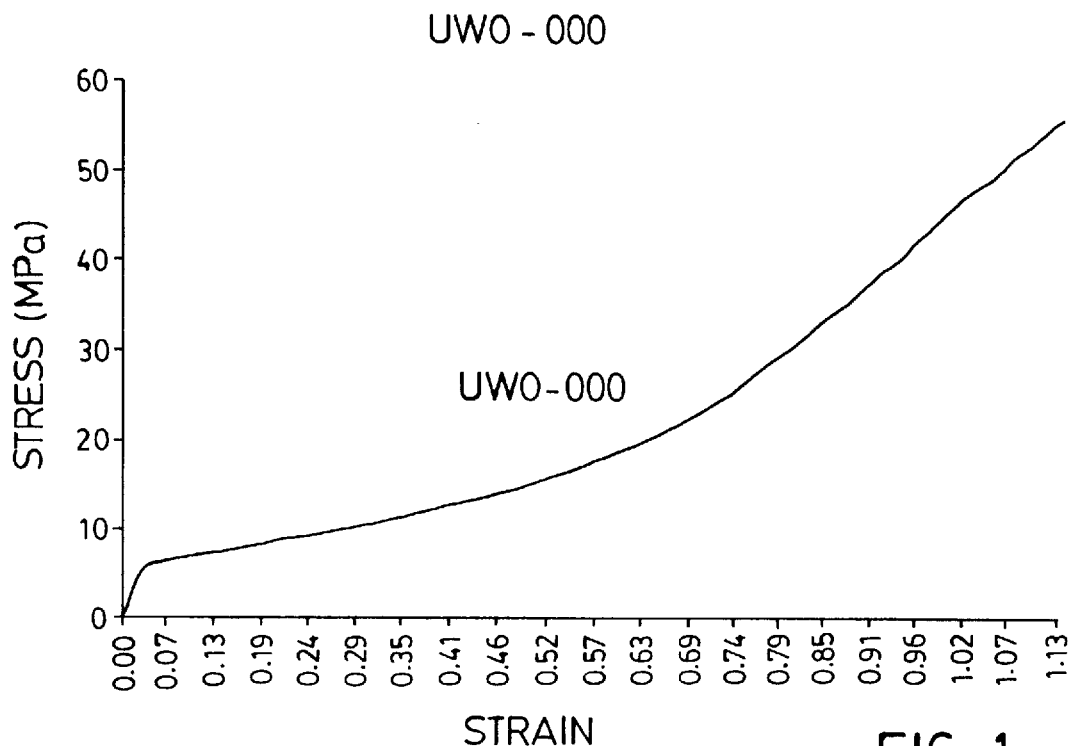
FIG. 1 shows a stress-strain curve for a sample UWO-000 produced in accordance with the present invention.

In preparing the wound dressings of the present invention, cellulose produced by the bacteria *Acetobacter xylium* (Cellulon™, NutraSweet Kelco Company, 2025 East Harbor Drive, San Diego, Calif., 92113-2123) was dissolved in a solvent system comprising dimethylacetamide and a lithium salt, preferably lithium chloride. The lithium chloride concentration in the solvent is in the range from about 5% to about 12%, and preferably about 9%. Concentration of cellulose in the resulting solution was in the range from about 2% to about 8%. The solution was filtered with 25 pm millipore filter. This ensured the removal of any undissolved cellulose before the solution was cast.

The solution is spread onto a solid smooth surface using a casting knife with a built-in gap width. Depending on the gap width of the casting knife used, solution films of a wide range of thickness can be made. After a drying period of between approximately 0–360 minutes, the solution film is then transferred into a gelation bath comprising water. Cosolvents and additives can also be added to the bath. Examples of these are alcohols, ketones and ethers that are miscible with water. The cosolvents are believed to assist in the formation of an open capillary system in the membrane to provide a porous structure. The coagulated film is then transferred into distilled water, rinsed thoroughly and then soaked in a bath comprising a humectant such as glycerol, polyvinyl alcohol, polyethylene glycol etc. followed by air drying. The role of the humectant is to displace water from the capillary structure and to replace it with a hygroscopic material having hydroxy groups.

To produce films of large surface area, casting may be done on a continuous casting machine which those skilled in the art will understand. This invention is further illustrated by the following non-limiting examples.

EXAMPLE 1

A 4% solution of cellulose produced by *A. xylinum* was prepared by the following procedure. Wet cellulose (Cellulon™) (40 g, cellulose content 17.85%) was soaked in distilled water (100 ml). After 24 hours, the cellulose was filtered and transferred into methanol (70 ml), stirred and filtered. This procedure was repeated three more times. After this, the cellulose was transferred into dimethylacetamide (70 ml), stirred and filtered. This procedure was repeated four more times. The cellulose was then dried in a vacuum oven until cellulose concentration was about 30–45%. The actual concentration of cellulose was determined gravimetrically by drying a sample in a vacuum oven at −100° C. The resulting cellulose was used to prepare the 4% cellulose solution in a solvent system of 9% lithium chloride in dimethylacetamide.

Cellulose solution films were prepared using a casting knife with a gap width of 100 μm. The films were coagulated in a water bath after a range of drying time of 0–240 minutes. A film, with a drying time of 0 minutes, coagulated in a 50% DMAc and 50% water bath was also prepared. The films were then solvent exchanged in a 10% glycerol solution and then were laid flat to air dry. Also a dense film was prepared by allowing the solvent to be completely removed by vacuum without the use of a water bath. Plant derived cellulose films were prepared in a similar manner for purposes of comparison. Inspection of these films are summarized in the following Table 2. All samples made in accordance with the present invention are labelled UWO-XXX-XX, the second three digits represents the drying time in minutes for that particular sample, and the last two digits designate the direction of draw of the cellulose solution during film preparation and may be either 00 or -90 corresponding to either being parallel to, or perpendicular to the direction of draw respectively.

TABLE 2

| Sample | Drying Time | Thickness | Appearance |
|---|---|---|---|
| UWO-000 | 0 | ~10 μm | clear |
| UWO-060 | 60 minutes | 10 μm | clear |
| UWO-240 | 240 minutes | 10 μm | clear |

Mechanical Properties of Prepared Films

Strips 5 mm×25 mm were cut from the cellulose films for testing, using a surgical blade and a template. The strips were cut from the film in both the draw direction and perpendicular to the draw direction. The thickness was measured using a lever apparatus which measures the displacement due to the thickness of the specimen. The displacement is converted to a measurement in mm. The measurement was accurate to ±0.001 mm. The mechanical properties of cellulose solution films were determined using an Instron tensile tester (Model 1125) with a load versus crosshead distance travelled setup. The gauge length of the specimen was recorded before the start of each test. The gauge length is the length of the specimen between each grip. At this point the specimen was straightened and the load was zero. Preconditioning was performed on each strip before testing to ensure repeatability of uniaxial tests. The specimens were loaded from 0-25 -0 g, for 5 cycles, at the same crosshead speed used for the mechanical tests. Load versus elongation was monitored for verification.

Five stress-strain tests were performed on each of different types of specimens, at extension rates of 5 mm/min with a 500 g load cell. The tensile tests were performed on dry samples. Stress-strain curves were obtained by straining the specimen from a load of 0 g to the load at which failure occurred. The engineering stress was obtained from the recorded load and defined as:

Stress (MPa)=(Load(g)*9.81 (g/m$^2$))/(width(mm) *thickness(mm)* 1000) where load in g is recorded from the load cell, width and thickness is the initial dimensions of the specimen.

Engineering strain is defined as;

Strain=1−lg/lg where I is the length and 1 g is the recorded gauge length at zero load. The stress-strain curves were plotted as strain versus stress (MPa). The curves for specimen cut in the x and y direction were both determined. The ultimate tensile strength (stress at failure), the elastic modulus (slope of the initial curve) and percent elongation (maximum strain) were calculated from these curves.

A typical stress strain curve of the cellulose films with zero drying time is shown in FIG. 1. These cellulose films exhibited small strain increments in the elastic lower stress regions followed by increased strain increments in the higher plastic stress regions. The results of the stress-strain tests for the cellulose films with various drying times and commercial cellulose Biofill™, a trademark of Biofill Productos Biotechnologicos, Curritiba, Parana, Brazil, are presented in Table 3.

TABLE 3

| Sample | Ultimate Tensile Strength (Mpa) | Elastic Modulus (MPa) | Fracture Strain (%) |
|---|---|---|---|
| UWO-000-00 | 53.2 ± 3.5 | 276.8 ± 28.6 | 98.4 ± 5.4 |
| UWO-000-90 | 37.2 ± 2.9 | 206.3 ± 23.5 | 143.2 ± 6.2 |
| UWO-060-00 | 54.8 ± 8.2 | 295.4 ± 31.2 | 99.1 ± 3.5 |
| UWO-240-00 | 38.3 ± 5.3 | 297.7 ± 29.5 | 38.8 ± 4.1 |
| UWO-1200-00 | 39.7 ± 4.3 | 293.8 ± 31.5 | 37.3 ± 2.2 |
| BIOFILL ™ | 159.4 ± 6.9 | 1678 ± 5.1 | 15.8 ± 2.3 |

The mechanical properties of the specimens varied with the drying time. From Table 3, the measured properties show that an increase in the drying time caused a decreased fracture strain and an increased elastic modulus. The zero drying time had the highest strain to fracture and the lowest elastic modulus. This resulted in a sample with elasticity and extensibility.

Figure 2:
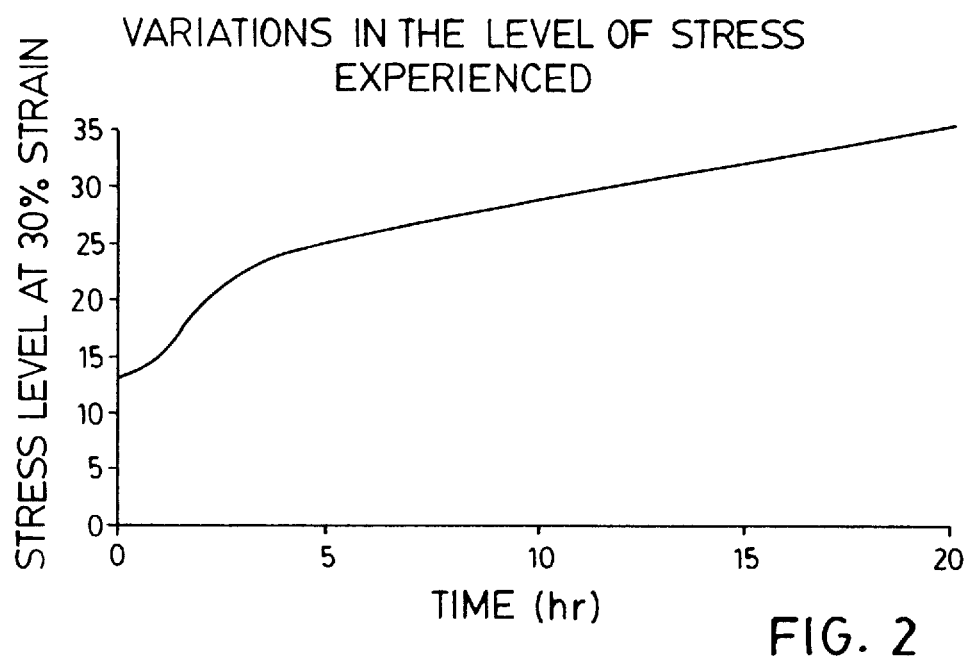
FIG. 2 is a plot of stress at a constant strain level of 30% for the samples prepared with various periods of drying time.

As the drying time increased the level of stress at a particular level of strain increased. This result is illustrated in FIG. 2 where stress is plotted at a constant strain level of 30% for the samples prepared with various periods of drying time. The level of stress steadily increased as the drying time during the preparation was increased, it can be concluded from the observed results that the mechanical properties of the cellulose films can be controlled by the preparation conditions. As the drying time increases, the stiffness of the films increased and the extensibility decreased.

The fracture strain of the films ranged from 40 % to over 100%. The results can be interpreted in terms of polymer organization in the cast cellulose film. Initially following casting, the polymer chains are loosely aligned. Long drying times allow the polymer chains to become more organized, leading to an increase in stiffness and a decrease in fracture strain. The strong hydrogen bonding of cellulose leads to this organization. Some of the prepared samples showed adequate strength and extensibility to be used as a wound dressing.

Figure 3:
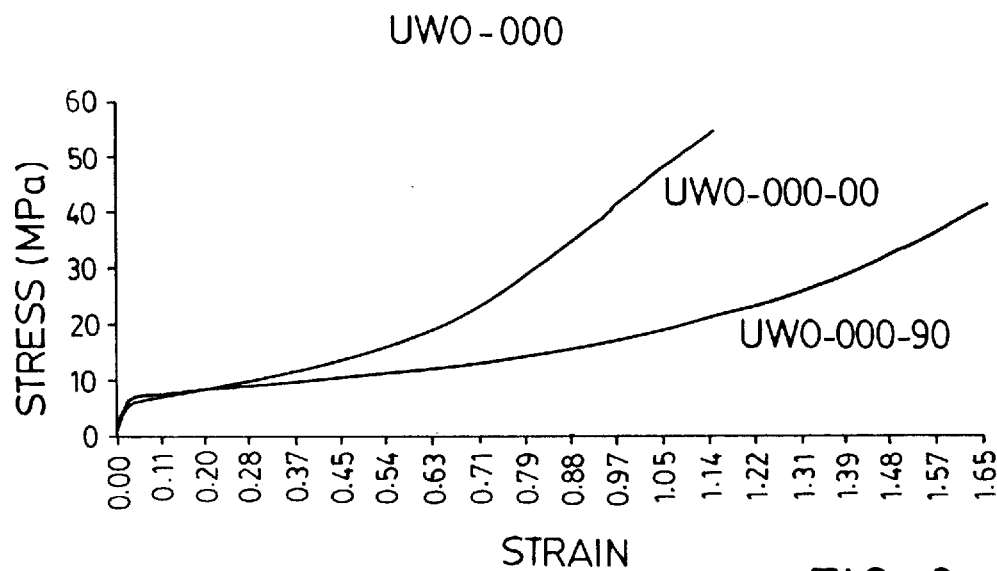
FIG. 3 shows stress-strain curves for a sample (UWO-000) of a microbially produced cellulose membrane produced in accordance with the present invention in both the direction of draw (UWO-000-00) and perpendicular to the direction of draw (UWO-000-90)

Referring now to FIG. 3, the stress-strain curve for sample UWO-000-00 produced according to the present invention in both the direction of draw (UWO-000-00) and perpendicular to the direction of draw (UWO-000-90). As may be seen from FIG. 3 the cellulose films exhibited an anisotropic behaviour. The films are hence stronger in the direction of draw but more elastic perpendicular to the direction of draw.

In other words, the draw direction exhibited a higher strength and the direction perpendicular to the draw direction exhibited a higher amount of extensibility.

Linear polymers such as cellulose tend to line up in the direction of draw. Mechanical strength in this direction is proportional to the inherent strength of the polymer chain. Perpendicular to the draw direction, neighbouring polymer molecules are held together mainly by intermolecular hydrogen bonding. Hence, it would be expected that mechanical properties of the film are anisotropic. The observed results indicate that the polymer chain is stronger than the intermolecular hydrogen bonds between neighbouring polymer chains. It is interesting to note that human skin also exhibits anisotropic behaviour.

Figure 4:
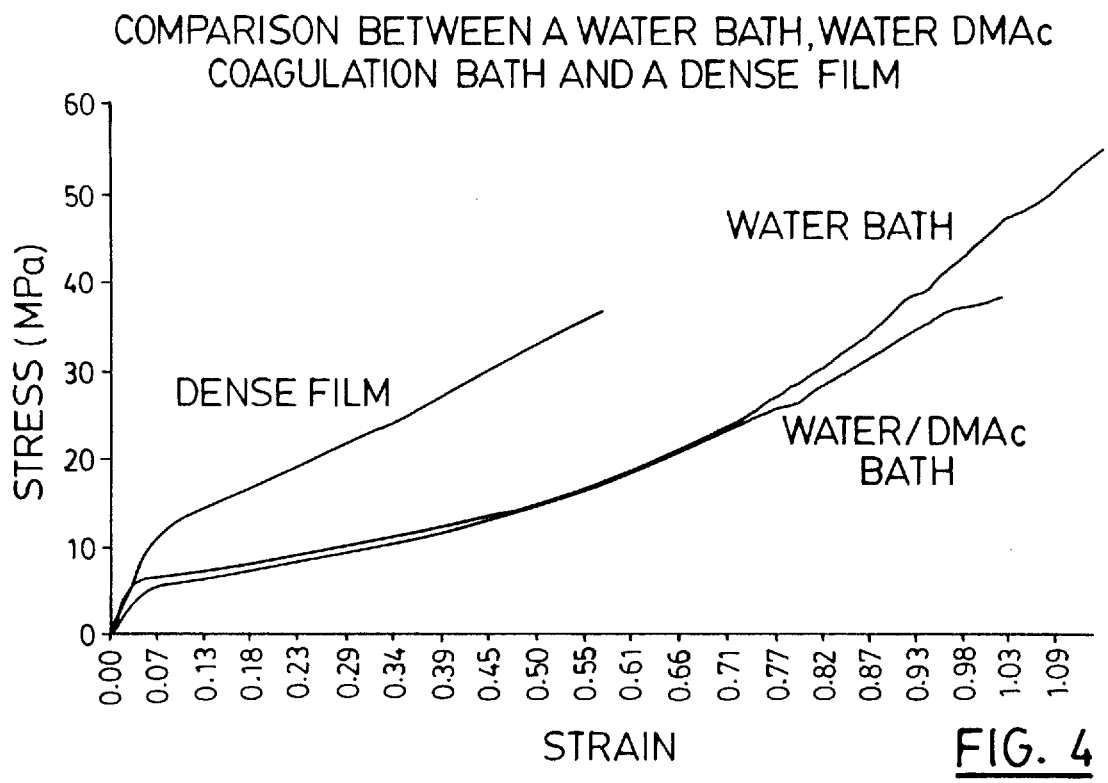
FIG. 4 shows the stress-strain curves for the films soaked in different bath mediums.

The results of a typical stress-strain curve for the films soaked in the different bath mediums is illustrated in FIG. 4. It is clear that there is no clear difference in the samples. The DMAc provided no improvement in the mechanical properties. The film that was allowed to dry completely to form a dense film showed clear differences in its mechanical properties compared to the film soaked in the water bath. As shown in FIG. 4, the dense film has both lower stress and strain values and hence was less suitable, in terms of mechanical properties, for the purpose of a wound dressing.

The different bath mediums used in the preparation conditions had no clear effect on the mechanical properties. Previous reports indicated that for some films, additional swelling in a solvent can improve its mechanical properties, see W. Zhao et al. Chemtech, March 32, (1996). In the present preparation, DMAc had no further swelling effect to alter the mechanical properties of the film The film that was prepared without a bath medium and was allowed to dry to form a dense film had a lower level of elasticity and strength. Water was used as the bath medium of choice for the wound dressing preparations.

Figure 5:
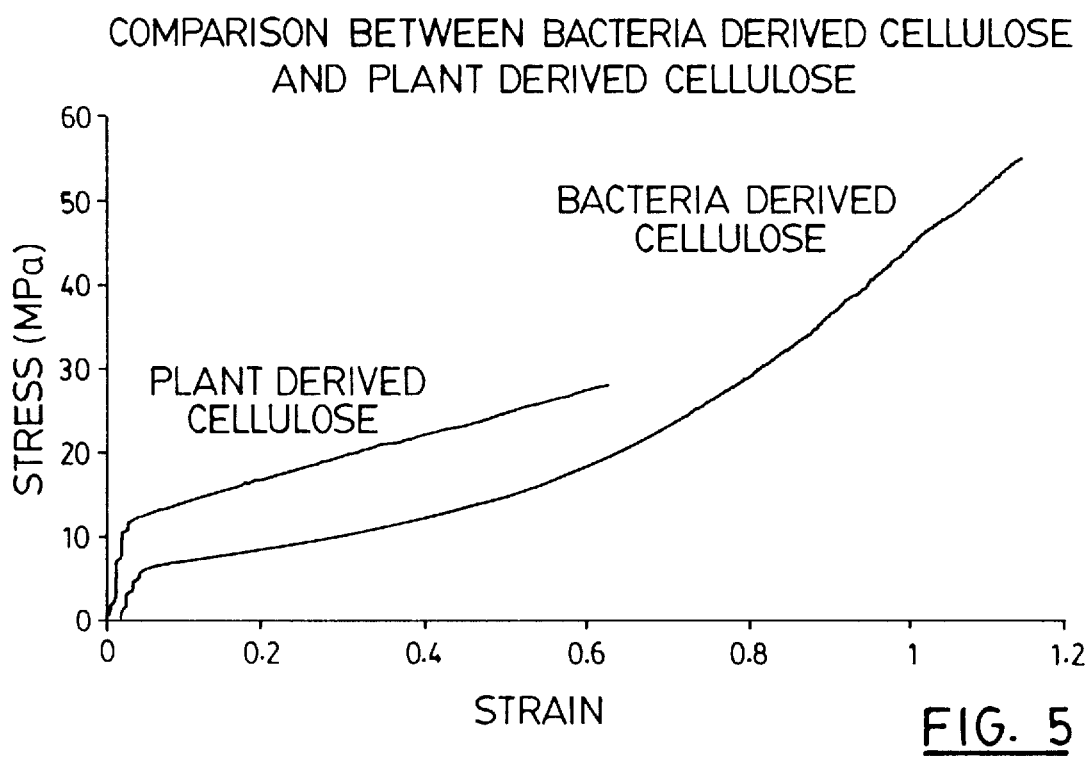
FIG. 5 compares the mechanical properties of a film prepared from a plant derived cellulose, with zero drying time, and a bacteria derived cellulose according to the present invention.

The mechanical properties of a film prepared from a plant derived cellulose, with zero drying time, is shown in FIG. 5. The film was prepared under conditions identical to the preparation conditions of the bacterial derived cellulose. The comparison between the bacteria source cellulose film and the plant source cellulose derived film revealed that they have very different mechanical properties. The plant derived cellulose films were stiffer and had lower ductility. It can be concluded that the bacteria derived cellulose produced films possess more suitable mechanical properties as a wound dressing than the plant derived cellulose films.

The Comparison of Mechanical Properties of The Prepared Films with Human Skin and Commercial Products Human skin consists of collagen fibres randomly arranged in layers. Quantitative analysis of human abdominal skin revealed that there is an overall preferential orientation of fibres across the abdomen. This is the direction of minimum extensibility. Thus skin tissue shows mechanical anisotropy. As shown previously in FIG. 3 films prepared by the present method exhibit anisotropic behaviour and therefore is consistent with the properties of human skin.

A general quantitative analysis of the mechanical properties of human skin is difficult due to the differences in human skin at different ages. With increasing age the skin becomes less extensible and the tensile strength increases. Studies reveal age related changes in the form of the collagen fibres of the dermis, which accounts for their decreased mobility in elderly skin. In children's skin, the fibres are loosely arranged with less connections between the fibres. This accounts for the increased extensibility. On average, an adult's abdominal skin has a tensile strength of 7 MPa and an elongation of 80 percent.

Figure 6:
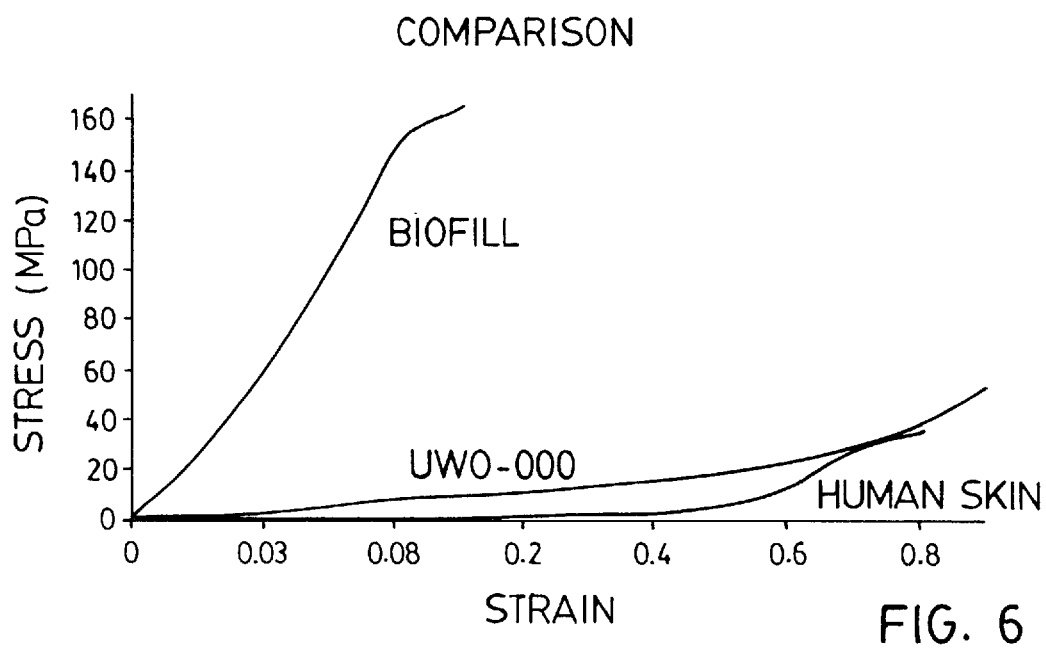
FIG. 6 shows the fracture strain, measured using an Instron tensile tester, for the sample UWO000-00 compared with that of human skin and Biofill™, a cellulose wound dressing derived from the cellulose pellicle produced by *A. xylinum*.
Figure 7:
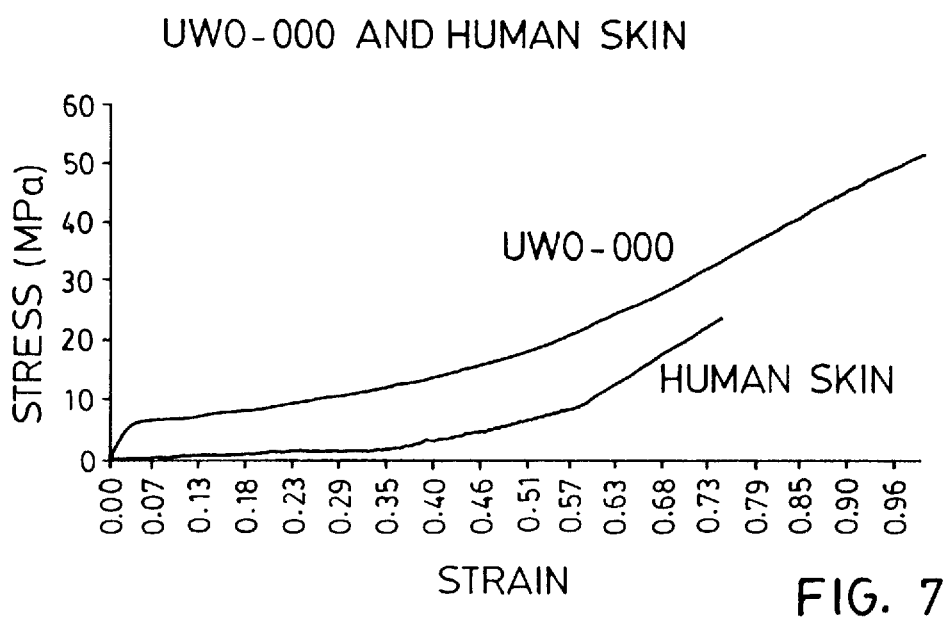
FIG. 7 shows the fracture strain data of FIG. 6 for the sample UWO-000-00 on an expanded scale.

The elastic modulus of the proposed wound dressing determines the ability of the sample to be used as a wound dressing on areas of high mobility. It is thus suitable for use on wounds in areas of high mobility. FIG. 6 compares the fracture strain for the sample UWO-000-00, human skin and Biofilm™, a cellulose wound dressing derived from the cellulose pellicle produced by A. xylinum. It can be seen that UWO-000-00 has very similar fracture strain to the human skin but much higher than that of Biofill™. A closer comparison between UWO-00-00 and human skin is shown in FIG. 7. The higher strength and fracture strain exhibited by UWO-000-00 than human skin is advantageous when films produced by the present method are used as wound dressings.

Figure 8:
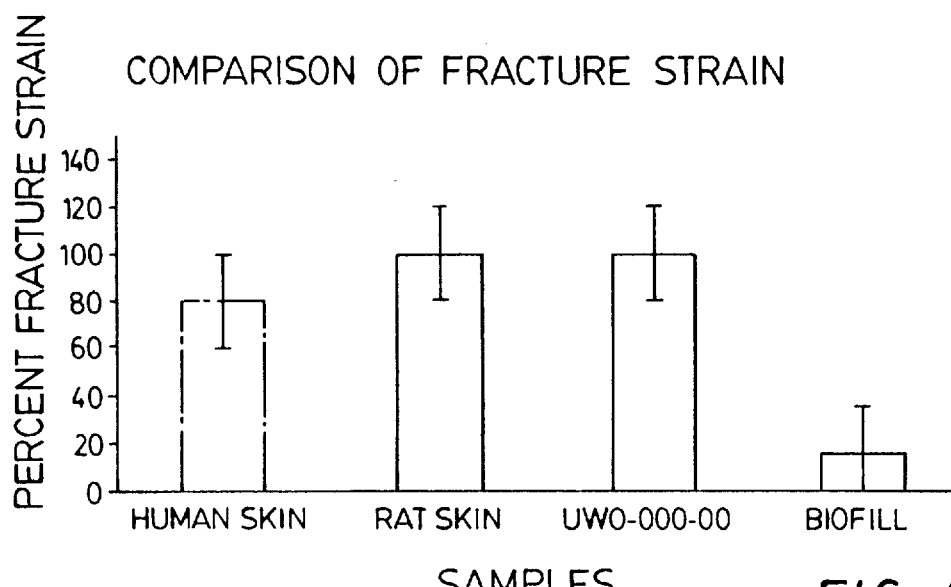
FIG. 8 compares the fracture strain of human skin, rat skin, sample UWO-000-00 and commercial Biofill.

FIG. 8 shows a comparison of the fracture strain of the cellulose film (UWO-000-00), Biofill (commercial product), rat skin and human skin (see "The Biomedical Handbook" Yannas. CRC Press Inc. p. 2025–2045, 1995 and R. Hut, J. Biomechanical Engineering, 111, p. 136, 1989). The fracture strain of the UWO-000-00 cellulose film is very similar to that of the rat skin and human skin and greatly exceeded that of the commercial product Biofill. Therefore the dressing produced by the present invention is thus much more suitable for use on wounds in areas of high mobility due to its improved extensibility and elasticity.

The cellulose that makes up the present films produced according to the present invention and the Biofill product were both derived from the bacteria *Acetobacter xylinum*. The results show clear differences in the mechanical properties exist between them. The difference in mechanical properties and appearance is due to the cellulose film preparation process. Regeneration of cellulose films from a cellulose polymer solution allows for better control of the resulting film properties.

Water Permeation Studies

An Amicon ultrafiltration cell, model 8050, was used to determine water permeation rates. The cell was lined with the sample and subjected to water at various pressures. At the end of a two minute time period, the mass of the water was measured. This procedure was repeated several times until a constant mass was reached. This was performed at several different pressures. The permeation rates were calculated from the data and recorded in units of $g/m^2$-hr, where g represents the mass in grams, hr is the time in hours and m is size of the film in meters. These results were then used to estimate the water vapour permeance rates.

Figure 9:
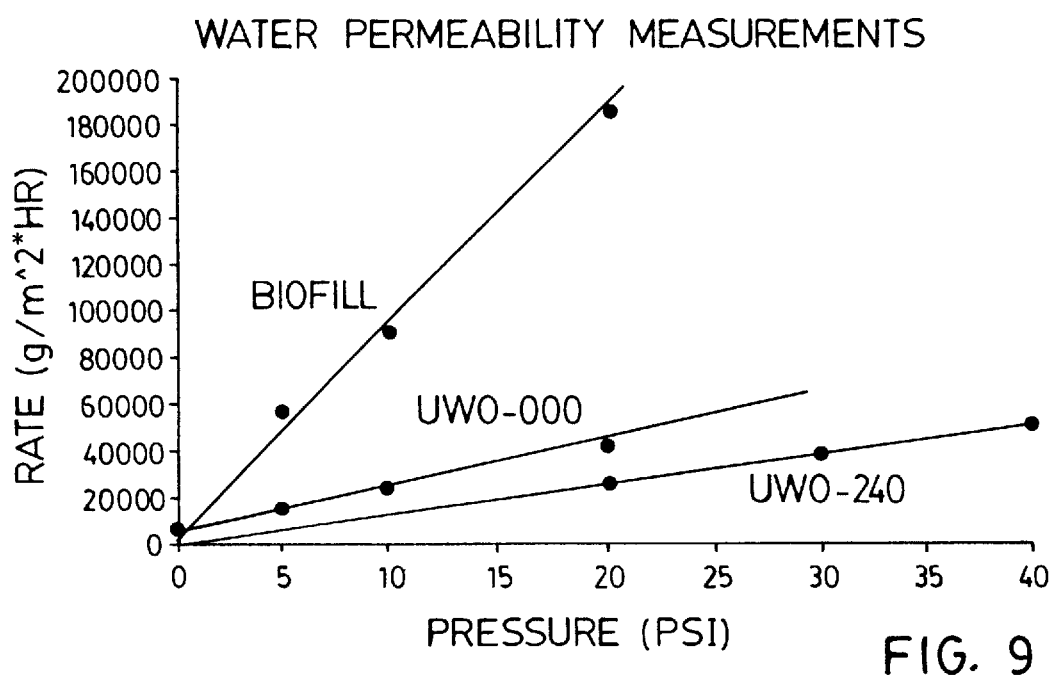
FIG. 9 compares the rates of water permeation of the cellulose films (UWO-000, UWO-240) prepared according to the present invention compared with the Biofill dressing of FIG. 6, the membranes were subjected to pressure in a permeation cell and water permeation rates were determined.

Water permeation rates were determined for the UWO-000 sample preparations. Referring to FIG. 9, for comparison, the permeation rates for a commercial wound dressing, Biofill, was also measured. It can be observed from the results in FIG. 9 that the films are permeable to water under pressure. A ratio between these two results and the water vapour permeance value from the literature for Biofill was used determine the water vapour permeance value for the UWO sample. The samples have a lower rate compared to Biofill. The results of the calculated water vapour transmission rates shown in Table 4 indicate an adequate level of permeation, see for example A. M. Gatti et al. J. Materials Science in Medicine, 5, 190 (1994) and M. Jonkman et al., Biomaterials 9, 263 (1988).

TABLE 4

Water Vapour Permeation

| Sample | Water Vapour Permeation (g/kPa*hr*m$^2$) |
| --- | --- |
| UWO-000 | 8.2 |
| Biofill ™ | 31 |
| Human Skin | 4 |
| Op-Site ™† | 11 |

†trademark of Smith & Nephew

A wound dressing should limit excessive evaporative water loss and desiccation of the wound to promote healing. However, a wound dressing must allow the passage of some water vapour to prevent excessive accumulation of exudate, which might cause the separation of the dressing from the wound. The results in Table 4 show that the water vapour permeance for the wound dressing produced in accordance with the present invention was lower than the two commercial products and is closer to human skin. The water vapor permeation data for human skin and the commercial product Op-Site is disclosed in M. F. Jonkman et al. Biomaterials, Vol. 9, p263–267, 1998. The water vapor transmission data for the commercial product Biofill is disclosed in A. M. Gatti et al., Journal of Material Science: Materials in Medicine, Vol. p.190–193, 1994.

Sterilization And Depyrogenation

The ability of the cellulose film to withstand both sterilization and depyrogenation processes are necessary and important steps towards making a biomedical device. Often biomedical polymers have lower thermal and chemical stability than other materials such as metals and ceramics and therefore they are harder to sterilize using conventional techniques. For any material used as a wound dressing, it must be free from pyrogens, bacteria and any possible contaminants that will interfere with the healing process. It is therefore important to study the effect of sterilization and depyrogenation on the properties of the cellulose films.

Figure 10:
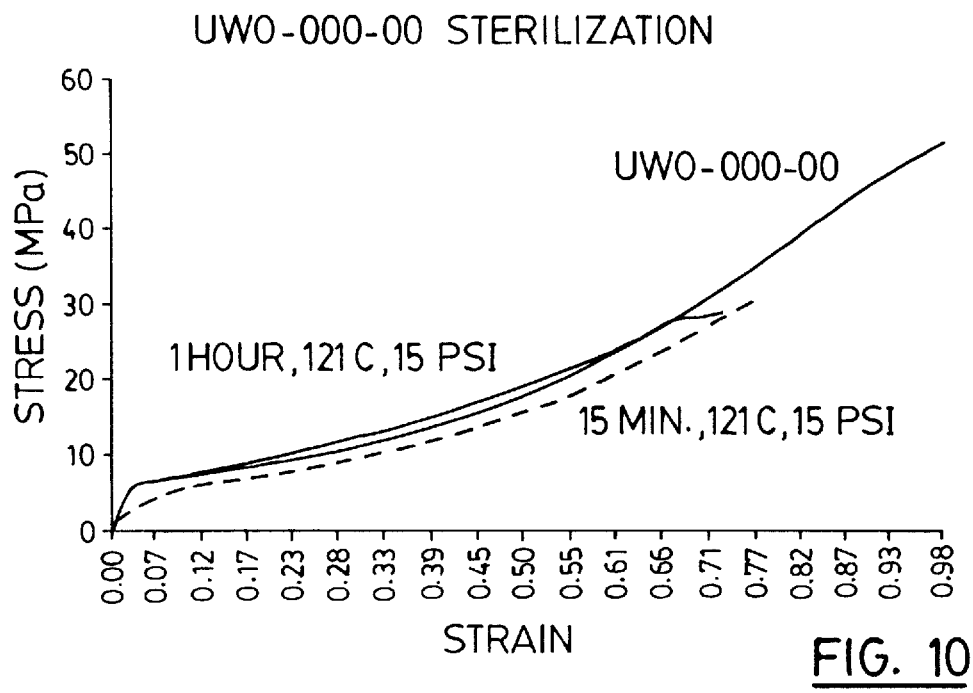
FIG. 10 shows the effect of sterilization on the stress-strain behaviour of the films produced according to the present invention.

The samples were steam sterilized by autoclaving in excess glycerol. The glycerol acts as a humidient to ensure that the structural and dimensional integrity is maintained. A series of runs for 15 minutes and 1 hour at 121° C. and a pressure of 15 psi were used to determine the effects. The stress-strain relationships of the sterilized samples were determined and compared to the untreated samples. The results shown in FIG. 10 indicate that the films can be sterilized without any substantial change in their desirable mechanical properties. It can be concluded that the samples were able to withstand sterilization and depyrogenation without any significant changes to the mechanical properties.

Figure 11:
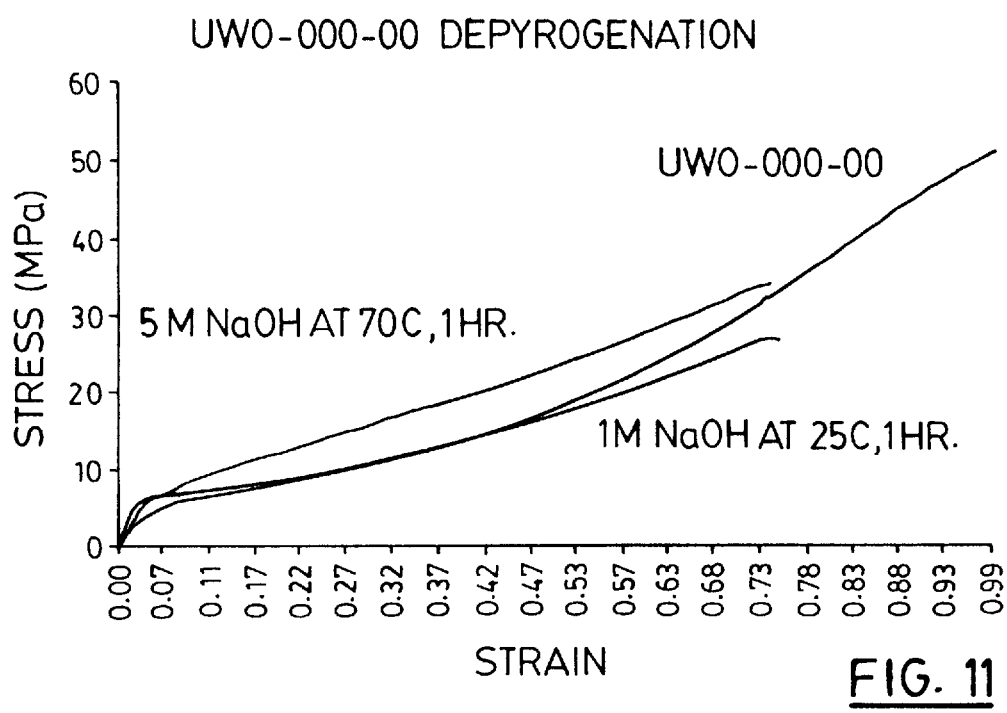
FIG. 11 shows the effect of depyrogenation on the stress-strain behaviour of the films produced according to the present invention.

The samples were depyrogenated in a 1M and 5M concentrated NaOH solution for 1 hour at 25° C. and 75° C., respectively. Following depyrogenation, the stress-strain relationships of the treated and untreated samples were compared. The results shown in FIG. 11 indicate that these films can be depyrogenated with a strong alkaline sodium hydroxide solution at an elevated temperature without any substantial change in their desirable mechanical properties.

Biocompatibility Tests

Figure 12:
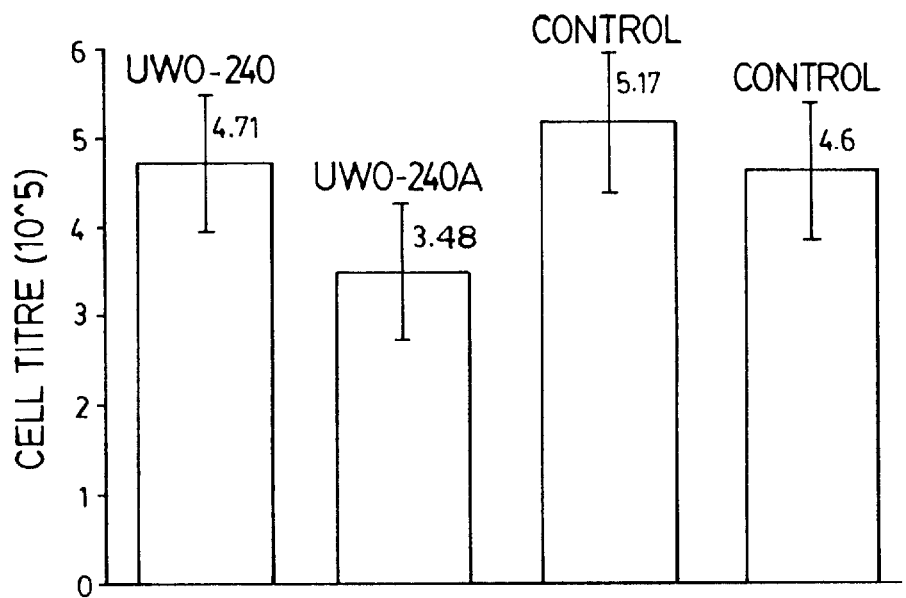
FIG. 12 shows the results of the biocompatibility studies with the films of the present invention compared to controls.

Friend erythroleukemia cells were grown in the presence and absence of the cellulose film samples. The cells were incubated in Iscoves medium at 37° C. for 3 days. Cell counts were done with a hemacytometer with three independent measurements taken per sample. A total of 1000 cells were counted for each sample. No cell lysis was observed. Results collected in Table and FIG. 12 indicate that the samples do not affect normal cell growth.

TABLE 5

Biocompatibility Results

| Sample | Cell Titer |
| --- | --- |
| Control 1 | $5.17 \pm 0.67 \times 10^5$ |
| Control 2 | $4.60 \pm 0.67 \times 10^5$ |
| UWO-240 | $4.71 \pm 0.67 \times 10^5$ |
| UWO-240 A | $3.48 \pm 0.67 \times 10^5$ |

Further tests were performed to determine if fibroblasts could grow in the presence of the cellulose films. Mouse fibroblasts, 3TC cells, were placed in a petri dish in the presence of the samples. Over a period of time observations were performed, without any counts to determine the relative abundance of the fibroblasts. These observations confirmed that the mouse fibroblasts were able to grow on the samples. The biocompatibility of the UWO membranes was thus demonstrated by the ability of both the Friend erythroleukemia cells and mouse fibroblasts to grow in the presence of the samples.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents. It will be understood that the bacterially produced cellulose membranes disclosed herein may be used in most applications for which known cellulose membranes are used.

Therefore what is claimed is:

1. A method for producing a cellulose membrane from microbially produced cellulose, comprising the steps of: (a) providing a prepared microbially produced cellulose;
    (b) dissolving the cellulose into a solvent system comprising a lithium salt and dimethylacetamide;
    (c) casting the solution onto a surface and drying to produce a membrane;
    (d) coagulating the membrane in a gelation bath; and
    (e) incorporating a humectant into the membrane by solvent exchange.

2. The method according to claim 1 wherein the microbially produced cellulose is produced by the bacteria *Acetobacter xylinum*.

3. The method according to claim 2 wherein said lithium salt is lithium chloride.

4. The method according to claim 3 wherein the lithium chloride concentration is in the range of 5–12%.

5. The method according to claim 4 wherein the drying time is in the range of 0–240 minutes.

6. The method according to claim 5 wherein the gelation medium is water.

7. The method according to claim 6 wherein the gelation medium is water and a cosolvent effective to assist in formation of a porous network in the cellulose membrane.

8. The method according to claim 7 wherein the cosolvent is a ketone, an alcohol or an ether that is miscible with water.

9. The method according to claim 3 wherein the humectant is selected from the group consisting of glycerol, polyvinyl alcohol or polyethylene glycol.

10. The method according to claim 2 wherein said step of providing the prepared microbially produced cellulose comprises soaking said cellulose in distilled water for an effective period of time, filtering and transferring said cellulose to methanol solution, stirring and filtering, transferring said cellulose to a solution of dimethylacetamide, stirring and filtering, drying in a vacuum oven until cellulose concentration is in the range from about 30 to about 45%.

11. A cellulose membrane produced by a process comprising the steps of:
   (a) providing a prepared microbially produced cellulose;
   (b) dissolving the cellulose into a solvent system comprising a lithium salt and dimethylacetamide;
   (c) casting the solution onto a surface and drying to produce a membrane;
   (d) coagulating the membrane in a gelation bath; and
   (e) incorporating a humectant into the membrane by solvent exchange.

12. The cellulose membrane according to claim 11 wherein the microbially produced cellulose is produced by the bacteria *Acetobacter xylinum*.

13. The cellulose membrane according to claim 12 wherein said lithium salt is lithium chloride.

14. The cellulose membrane according to claim 13 wherein the lithium chloride concentration is in the range of 5–12%.

15. The cellulose membrane according to claim 14 wherein the drying time is in the range of 0–240 minutes.

16. The cellulose membrane according to claim 15 wherein the gelation medium is water.

17. The cellulose membrane according to claim 16 wherein the gelation medium is water and an cosolvent effective to assist in formation of a porous network in the cellulose membrane.

18. The cellulose membrane according to claim 17 wherein the cosolvent is a ketone, an alcohol or an ether that is miscible with water.

19. The cellulose membrane according to claim 13 wherein the humectant is selected from the group consisting of glyceryl, polyvinyl or polyethylene glycol.

20. The cellulose membrane according to claim 12 wherein said step of providing the prepared microbially produced cellulose comprises soaking said cellulose in distilled water for an effective period of time, filtering and transferring said cellulose to methanol solution, stirring and filtering, transferring said cellulose to a solution of dimethylacetamide, stirring and filtering, drying in a vacuum oven until cellulose concentration is in the range from about 30 to about 45%.

21. A wound dressing, comprising:
   (a) a microbially produced cellulose membrane; and
   (b) a humectant incorporated into the cellulose membrane.

22. The wound dressing according to claim 21 wherein the microbially produced cellulose is produced by the bacteria *Acetobacter xylinum*.

23. The wound dressing according to claim 22 wherein the humectant is selected from the group consisting of glycerol, polyvinyl alcohol and polyethylene glycol.

24. The wound dressing according to claim 22 wherein said cellulose membrane is characterized by mechanical properties of tensile strength, elasticity, strength and extensibility comparable to said mechanical properties of human skin.

25. The wound dressing according to claim 22 wherein said cellulose membrane is characterized by a strain curve monotonically increasing in a range from about 0 to about 0.8 as a function of applied stress in a range of about 0 to about 40 MPa.

* * * * *

UNITED STATES PATENT AND TRADEMARK OFFICE
CERTIFICATE OF CORRECTION

PATENT NO.   : 5,846,213
DATED        : December 8, 1998
INVENTOR(S)  : Wan-Kei Wan It is certified that error appears in the above-identified patent and that said Letters Patent is hereby corrected as shown below:

Title page,
Item [54], ABSTRACT,
Line 1, replace "bum" with -- burn --.

Column 1,
Line 9, replace the word "bums" with -- burns --.
Line 28, replace the word "Bum" with -- Burn --.

Column 12,
Line 6, replace "polyvinyl" with -- polyvinyl alcohol --.

Signed and Sealed this

Twenty-fourth Day of September, 2002

Attest:

Attesting Officer

JAMES E. ROGAN
Director of the United States Patent and Trademark Office